United States Patent [19]
Rosenberg et al.

[11] Patent Number: 6,086,592
[45] Date of Patent: Jul. 11, 2000

[54] TISSUE GRAFT IMPINGEMENT DEVICE

[75] Inventors: Thomas D. Rosenberg, Holladay, Utah; Paul Alexander Torrie, Marblehead, Mass.

[73] Assignee: Smith & Nephew, Inc., Memphis, Tenn.

[21] Appl. No.: 09/003,615

[22] Filed: Jan. 7, 1998

[51] Int. Cl.$^7$ .......................................... A61F 5/00
[52] U.S. Cl. ................................. 606/86; D24/26
[58] Field of Search .................. 606/86, 87, 68, 606/80–90, 96–99, 72–98; 623/18, 13, 20; D24/26

[56] References Cited

U.S. PATENT DOCUMENTS

| D. 243,123 | 1/1977 | Shen et al. | D24/26 |
|---|---|---|---|
| D. 245,918 | 9/1977 | Shen | D24/26 |
| 4,057,858 | 11/1977 | Helfet | 623/20 |
| 4,134,158 | 1/1979 | Laure | 623/20 |
| 5,300,077 | 4/1994 | Howell . | |
| 5,380,331 | 1/1995 | Mikhail | 606/79 |
| 5,688,276 | 11/1997 | Shaffer | 606/73 |

FOREIGN PATENT DOCUMENTS

| 2744621 | 8/1997 | France . | |
|---|---|---|---|
| 2022422 | 12/1979 | United Kingdom | 606/88 |
| WO 94/00058 | 1/1994 | WIPO | A61B 17/16 |
| WO 96/22057 | 7/1996 | WIPO . | |

OTHER PUBLICATIONS

Arthrotek a Wholly Owned Subsidiary of Biomet, Inc. "Impingement–Free Tibial Guide System Surgical Technique", 1992.
Arthrotek An Integral Part of Biomet's Worldwide Team, "The One Step Guide for Positioning the Tibial Tunnel", One Step Tibial Guide System, 1996.
Smith & Nephew Endoscopy Division 1998 Products Catalog, "Knee Arthroscopy", pp. G1–G32.

*Primary Examiner*—Michael Buiz
*Assistant Examiner*—Lien Ngo
*Attorney, Agent, or Firm*—Fish & Richardson P.C.

[57] ABSTRACT

A device for determining possible impingement of a replacement tissue graft with a portion of a bone at a joint, the replacement tissue graft of the type to be inserted and secured within a bone passage at the joint. The device includes (1) an elongated support shaft having a longitudinal axis and (2) a head disposed at a distal end of the support shaft. The head has (a) an engagement passage having an axis, the engagement passage configured to engage a guide wire disposed within the bone; and (b) an impingement surface corresponding to the shape of a portion of the replacement tissue graft, the impingement surface spaced from the axis of the groove by a pre-determined distance corresponding to a dimension of the tissue graft.

22 Claims, 7 Drawing Sheets

TISSUE GRAFT IMPINGEMENT DEVICE

BACKGROUND OF THE INVENTION

This invention relates to tissue grafting.

An increasing number of surgical techniques are now performed arthroscopically. For example, arthroscopic procedures include reconstructing the anterior cruciate ligament (ACL) as well as the posterior cruciate ligament (PCL) in the knee.

When the ACL has ruptured and is nonrepairable, it is usually replaced in the knee using a substitute graft harvested from the patient or from a donor. For example, the substitute ACL graft may be selected, according to surgeon preference, from a portion of a patellar tendon having a bone block or plug at each end. Alternatively, artificial grafts formed synthetically or with a combination of artificial and natural material, such as a ligament augmentation device (LAD) to which tissue is sutured, may be used as a substitute graft. The term "graft" is used herein to encompass all of these tissue replacement items. Several ACL reconstruction techniques are described in U.S. Pat. No. 5,139,520, incorporated herein by reference.

Figure 1:
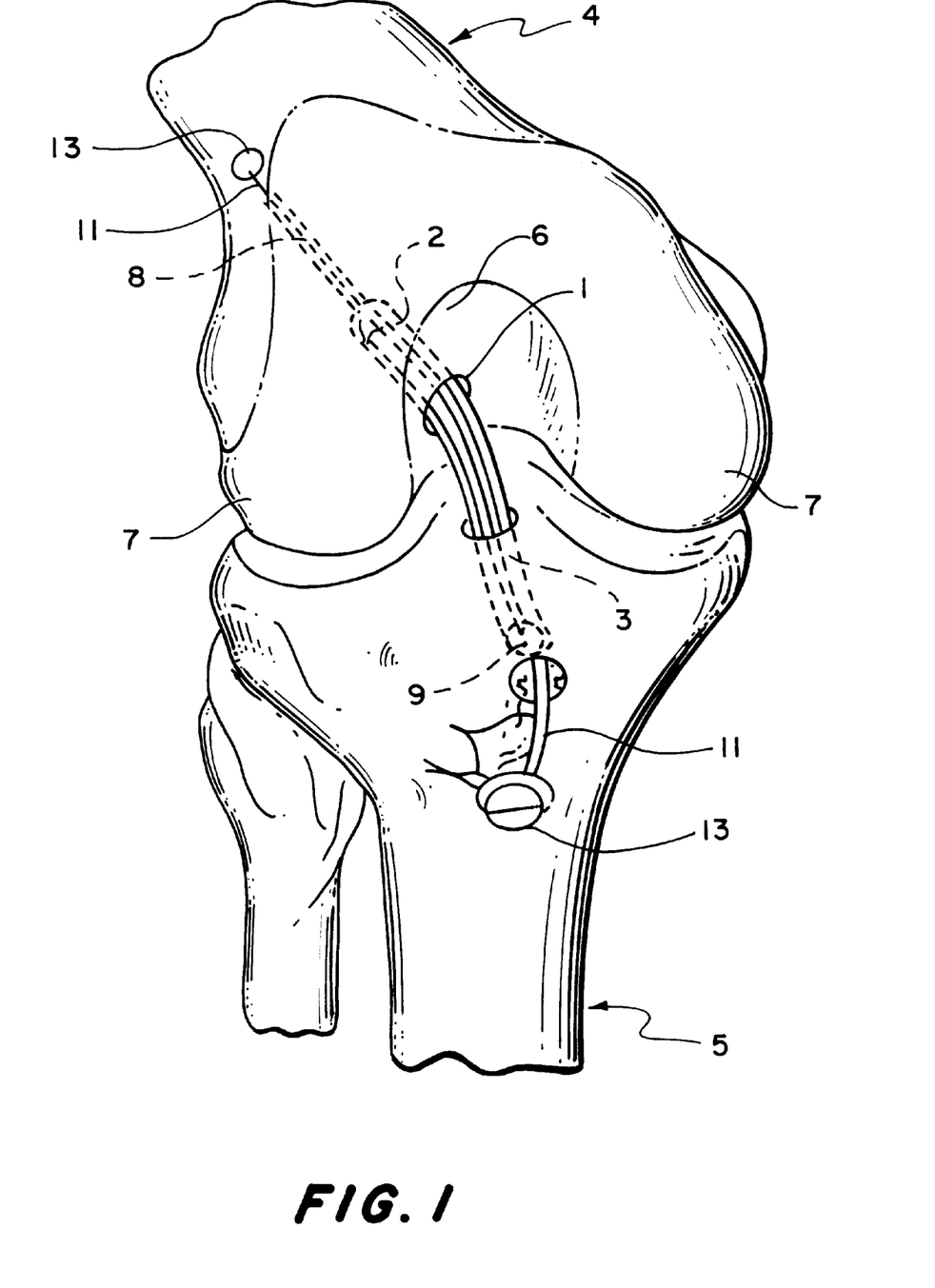
FIG. 1 shows a knee joint having an ACL replacement graft affixed to the femur and tibia.

Referring to FIG. 1, in one technique, an ACL graft 1 is inserted through bone passages 2 and 3 formed in a femur 4 and a tibia 5, respectively. These bone passages are formed by first using a drill tipped guidewire (not shown) to provide a hole extending through the bone followed by a larger drill which provides a closed-ended socket larger than the guidance hole and having a width at least as large as the width of the ACL graft 1. For example, with respect to femur 4, the drill-tipped guidewire initially forms a hole 8, and bone passage 2 is formed in the femur only after a larger drill is used to ream the original hole 8, so that graft 1 is allowed to pass through the roof of the intercondylar notch 6 (the portion of femur 4 flanked by two femoral condyles 7). Similarly, bone passage 3 in tibia 5 is formed by reaming with a larger drill only after a hole 9 is drilled by the guidewire. Subsequently, ACL graft 1 is secured in bone passages 2 and 3 by sutures 11 and suture anchors 13. The fully formed bone passage 3 passing through tibia 5 and accommodating ACL graft 1 is hereby referred to as the tibial tunnel.

A successful ACL graft reconstruction depends on the proper positioning of the tibial tunnel through which the graft passes. If the tibial tunnel is not correctly positioned, the graft may impinge on the roof of the intercondylar notch of the femur when the knee fully extends, potentially rupturing the graft. In order to properly locate the position of the tibial tunnel to be drilled so that the ACL graft passing through it will not impinge on the roof, tibial guide devices such as the ones described in U.S. Pat. No. 5,300,077 and PCT publication WO94/00058 are often used. These devices use the roof of the intercondylar notch as a reference point to position the guidewire for drilling the initial hole.

The surgeon can also relieve impingement of an ACL graft on the roof of the intercondylar notch by performing a notchplasty procedure in which a portion of the bone forming the roof of the notch is removed. In general, the surgeon removes a portion of the bone of a size large enough to prevent impingement.

SUMMARY OF THE INVENTION

The invention features an impingement device for determining possible impingement of a replacement tissue graft (e.g., an ACL graft) with a portion of a bone (e.g., a tibia) at a joint (e.g., a knee-joint), the replacement tissue graft of the type to be inserted and secured within a bone passage (e.g., a tibial tunnel) at the joint.

In a general aspect of the invention, the device includes an elongated support shaft having a longitudinal axis and a head disposed at a distal end of the support shaft. The head includes an engagement passage configured to engage a guidewire disposed within the bone and an impingement surface corresponding to the shape of a portion of the replacement tissue graft and spaced from an axis of the passage by a pre-determined distance corresponding to a dimension of the tissue graft.

Among other advantages, the impingement device allows a surgeon to determine whether the graft would impinge upon a portion of a bone before the bone passage for the graft is fully formed by the surgeon. For example, in an ACL reconstruction, the impingement device allows a surgeon to insert a tibial guidewire through the tibia and into the knee joint and attach the engagement passage of the device near the end of the guidewire. The knee joint is then fully extended and the impingement surface of the head is observed (via an endoscope, for example) to determine whether the surface contacts the roof of the intercondylar notch of the femur. The surgeon, therefore, is able to thereby determine whether impingement would occur if the tibial tunnel were to be drilled at the present position of the hole formed by the guidewire. In essence, the device serves as a surrogate ACL graft for determining impingement.

Unlike a tibial guide, the impingement device allows the surgeon to determine impingement given a selected position of the guidewire representing the future position of the tibial tunnel. This is a critical distinction, since the surgeon may wish to reference the tibial tunnel using anatomical landmarks other than the roof of the intercondylar notch of the femur. In contrast, known tibial guides require the surgeon to drill the initial hole, and consequently the tibial tunnel, in a specific position relative to the roof of the notch.

Embodiments of this aspect of the invention may include one or more of the following features.

In one embodiment, the head includes a detent mechanism which provides a spring-loaded fit between the engagement passage and guidewire, thereby facilitating engagement and disengagement of the passage with the guidewire. The detent mechanism includes a cantilever member defined by a slot formed in the head of the device.

In other embodiments, the engagement passage may be formed as a groove or a hole, either of which engages the guidewire via any suitable fit, including an interference fit, facilitates attaching and detaching and/or a sliding fit. When the passage is formed as a groove, the impingement device is attached and detached to and from the side of the guidewire. On the other hand, when the passage is a hole, the impingement device is slid over the distal end of the guidewire. The distal end of the support shaft can include a neck having an axis offset from the longitudinal axis of the shaft. In addition, the axis of the engagement passage can be at an angle (e.g., between 45° and 60°) from the axis of the neck so that the support shaft does not interfere with nearby bones.

The pre-determined distance between the axis of the engagement passage and the impingement surface can represent a dimension of the cross-sectional thickness of the replacement tissue graft (e.g., about 3 mm to about 6 mm). In addition, the impingement surface can be rounded to more closely approximate the shape of the tissue graft at the site of potential contact with the bone.

The device can include a second head at a second distal end of the shaft, the second head being used for a bilaterally symmetric joint. For example, the head at one end of the device can be used in a left knee ACL reconstruction, and the head at the other end of the device can be used in a right knee ACL reconstruction. The head of the device is configured to be removably detached from the distal end of the support shaft. A number of different size heads, each removably detached from the support shaft, can be provided, the size of the head related to the particular knee involved in the surgical procedure. The device may be made from a material such as stainless steel, titanium, or plastic.

In another aspect of the invention, a method includes steps for determining possible impingement of a tissue graft with a portion of a bone at a joint, the replacement tissue graft of the type which is to be inserted and secured within a bone passage at the joint.

The steps include: (a) inserting an end of a guidewire into a bone at a joint; (b) positioning a device at the end of the guidewire having an impingement surface; (c) extending the joint to full extension; and (d) determining if the impingement surface of the device contacts the bone, thereby determining possible impingement of the replacement tissue graft with the portion of the bone at the joint.

In certain embodiments, steps (b)–(d) above can also be repeated, with the surgeon removing a small portion of the bone responsible for graft impingement after determining if the impingement surface of the device contacts the bone, until no impingement occurs. Thus, the method minimizes the amount of bone that the surgeon needs to remove to alleviate impingement.

Fully forming bone passage is generally performed after determining whether impingement occurs.

Other advantages and features of the invention will be apparent from the following description and from the claims.

DETAILED DESCRIPTION

Figure 2A:
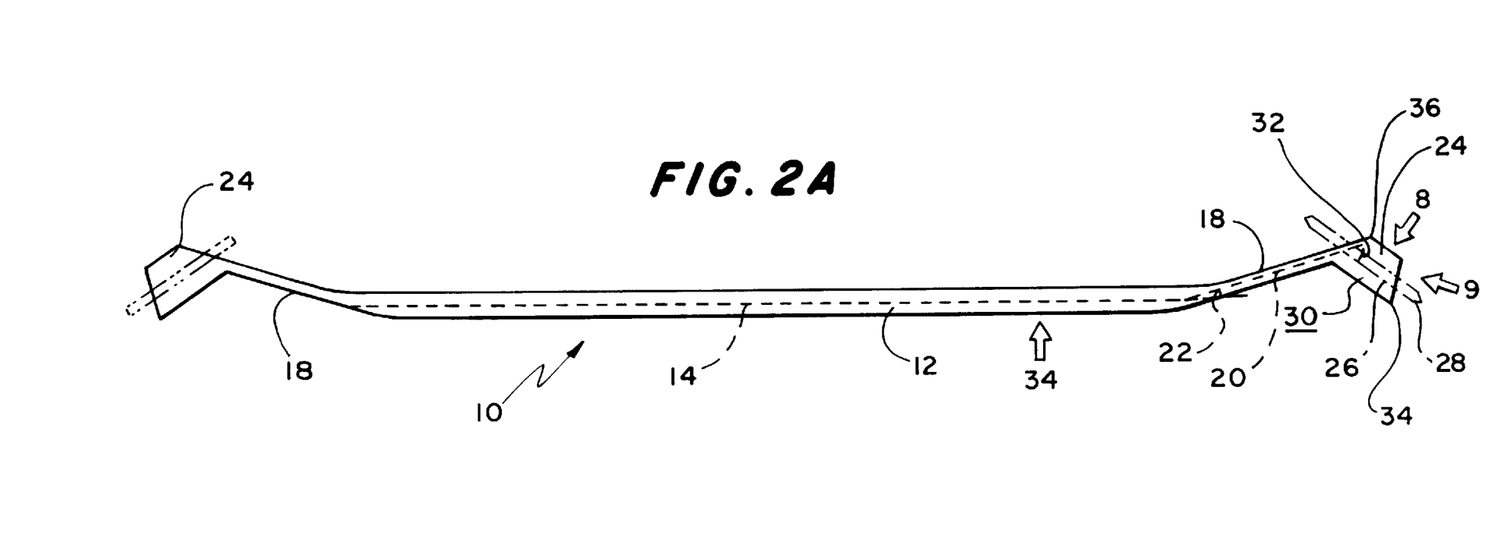
FIGS. 2A and 2B show perspective views of the impingement device. The view in FIG. 2B is indicated by the direction of arrow 34 in FIG. 2A.
Figure 2B:
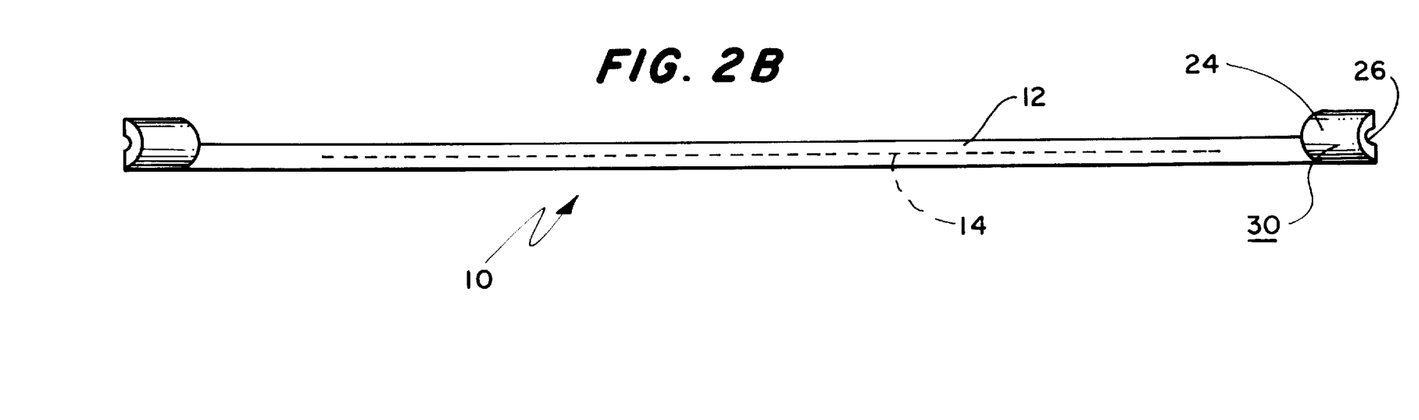

Referring to FIGS. 2A and 2B, an impingement device 10 includes an elongated support shaft 12 having a longitudinal axis 14. Impingement device 10 includes heads 24, 25 positioned at opposite ends of support shaft 12 and supported by narrowed neck regions 18 of shaft 12. Each of heads 24, 25 are mirror images of each other relative to plane 13 so that one head 25 is used in procedures involving the left knee and the other head 24 for the right knee.

Focusing on the right half of the device (e.g., used to determine possible impingement of a left knee ACL graft), narrowed neck region 18 has a neck axis 20 offset from longitudinal axis 14 of shaft 12 at an acute angle 22 to facilitate positioning of head 24 within the joint of the knee. Angle 22 helps ensure that, when the device is attached to a drill-tipped guidewire 40 (FIG. 4A), the device does not interfere with nearby portions of bone when initially positioning the impingement device into the joint (see FIGS. 4B and 4C and related discussion below).

Figure 3A:
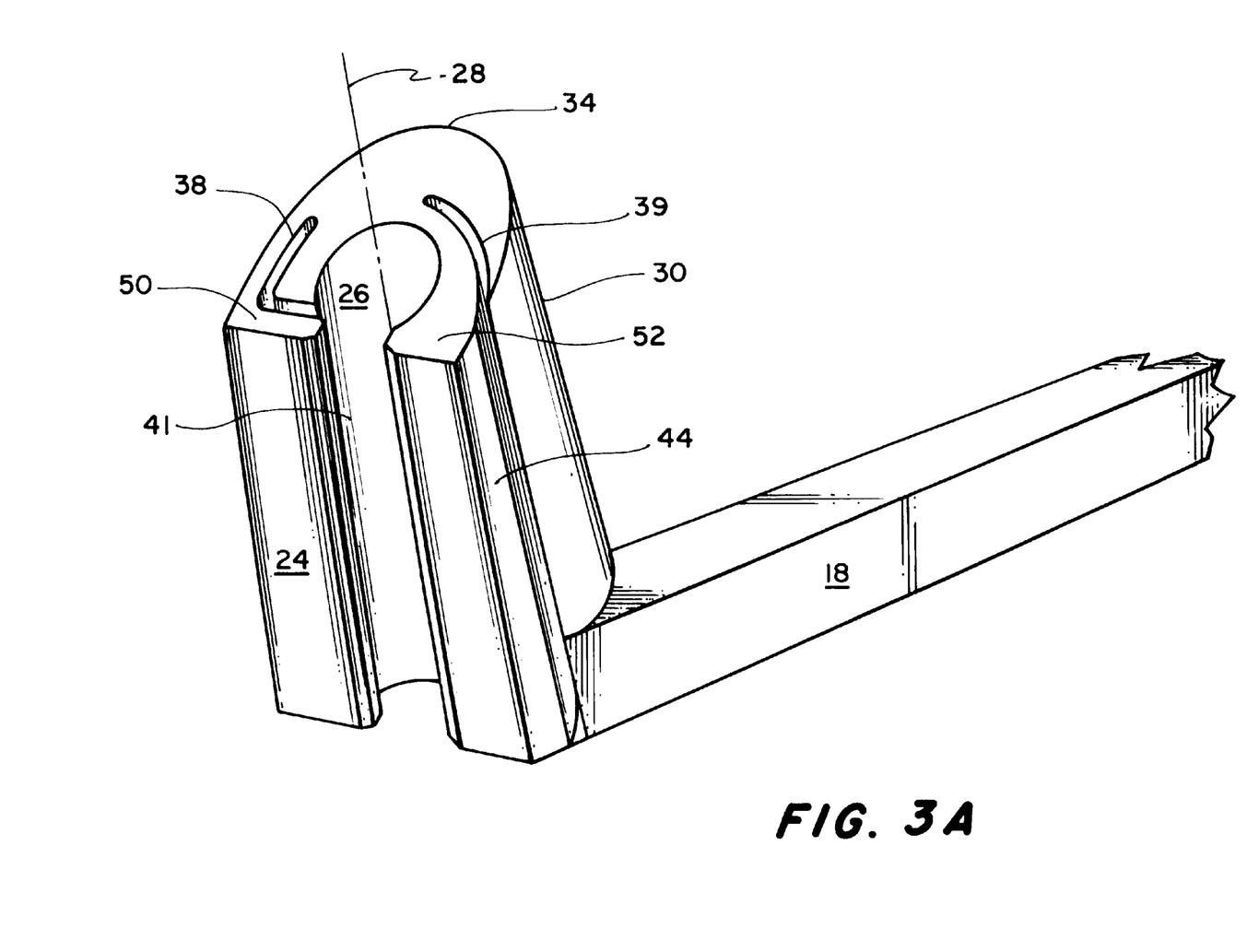
FIG. 3A shows the head of the device viewed from the direction of arrow 8 in FIG. 2A.
Figure 3B:
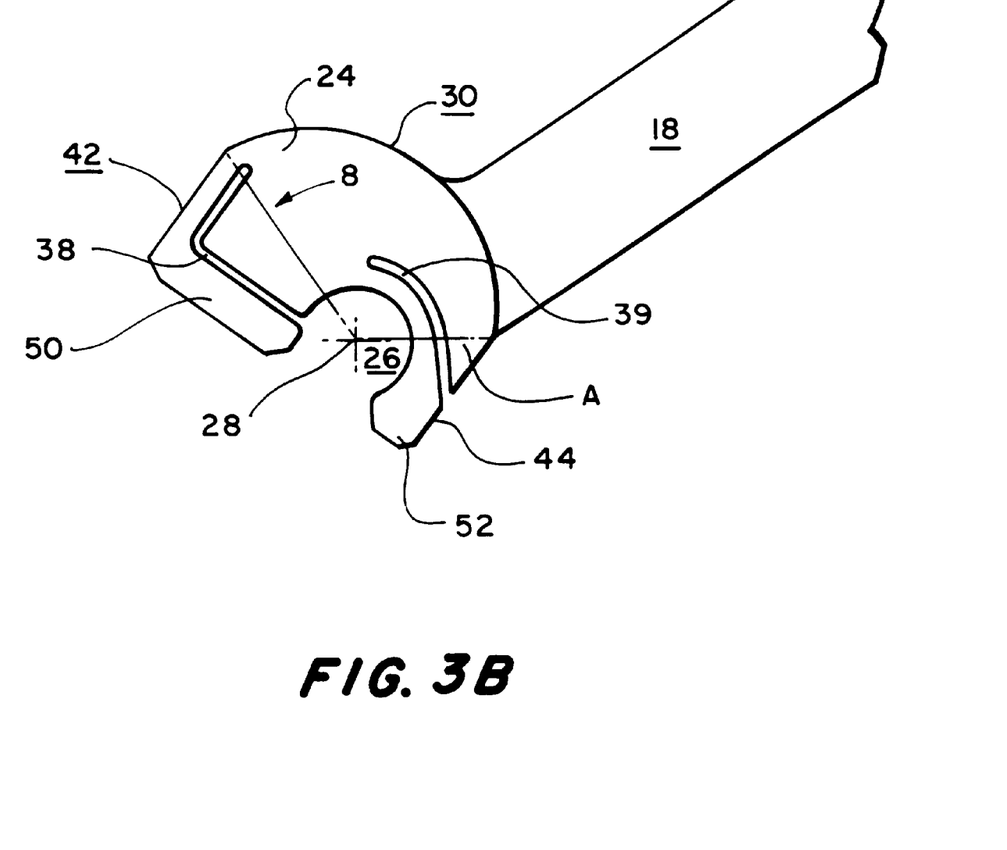
FIG. 3B shows the head of the device viewed from the direction of arrow 9 in FIG. 2A.

Referring to FIGS. 3A and 3B, the head 24 includes an engagement passage, here a groove 26, having a groove axis 28 and an impingement surface 30 bordered on one side by an edge 34. The groove axis 28 is at an angle 32 from neck axis 20 (e.g., any angle from 45° to 60°) which approximates the angle between a tibial plateau 48 (FIG. 4A) and axis 28 and positions axis 20 parallel to the tibial plateau. Angle 32, together with angle 22, helps ensure that the device does not interfere with nearby portions of bone not involved in possible impingement of graft 1 (FIG. 1). Groove 26 is sized to substantially surround the periphery of the distal end of drill-tipped guidewire 40 already positioned in the joint. Slots 38, 39 are formed to extend through head 24 so that groove 26 can be expanded sufficiently to provide a snap-fit engagement to the side and outer periphery of guidewire 40. In essence, slots 38, 39 provide a spring-like detent for ensuring reliable engagement of impingement device 10 to guidewire 40 while also permitting removal and replacement of the impingement device when necessary. Slot 38 extends from a wall 41 defining groove 26 towards an outer surface 42 of head 24, and bends upward towards impingement surface 30. Slot 39 extends from an outer surface 44 of head 24, and curves around the inner surface of groove 26. Thus, slots 38, 39 form cantilever members 50, 52, respectively for forming the spring-like detent mechanism.

The impingement surface 30 is spaced from groove axis 28, by a predetermined distance ranging from A to B (e.g., 3 mm to 6 mm), thereby providing an impingement surface which reflects the exterior dimensions of ACL graft 1 (FIG. 1).

Figures 4A, 4B:
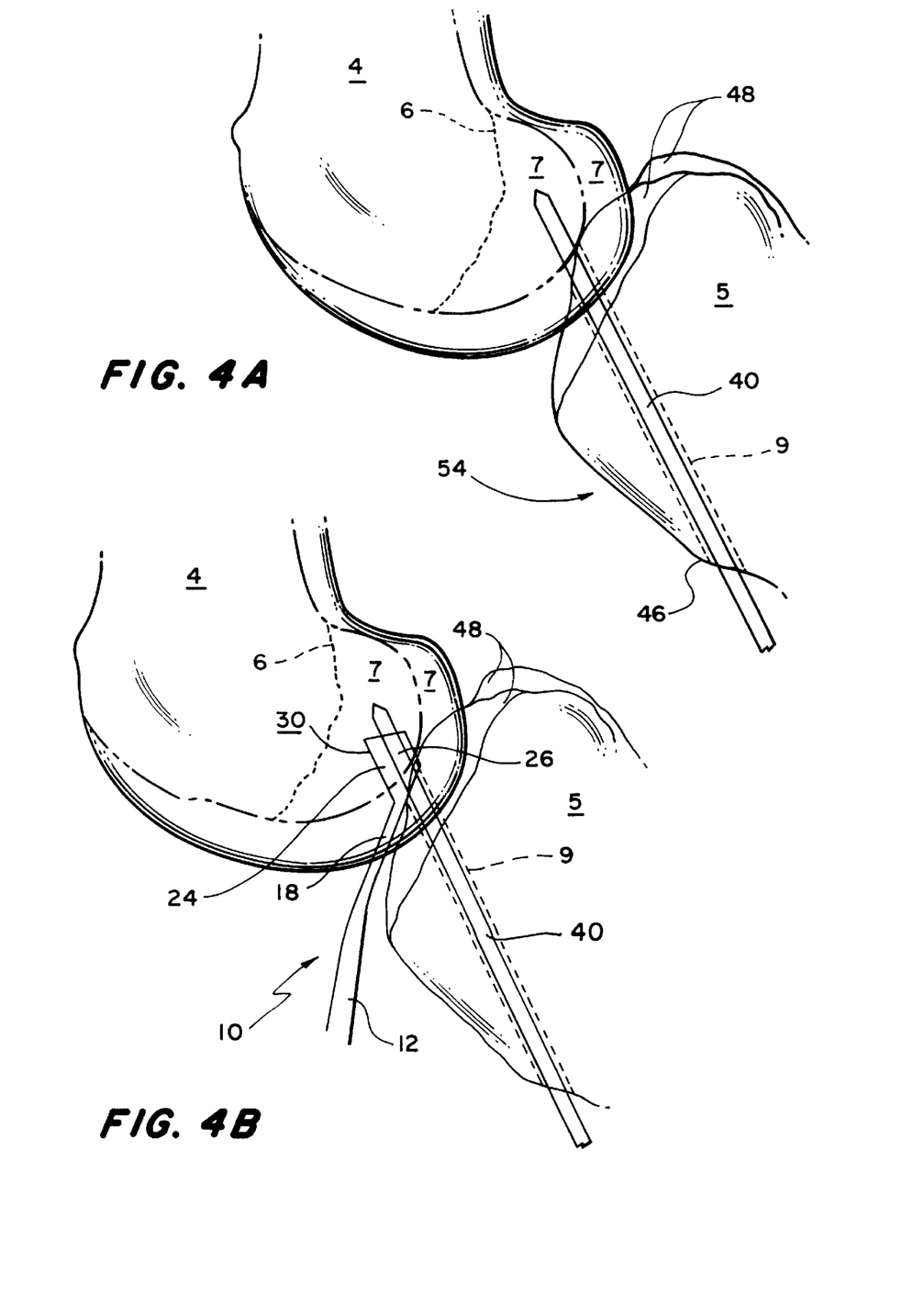
FIGS. 4A, 4B, and 4C illustrate a method of using the impingement device of FIGS. 2A and 2B.
Figure 4C:
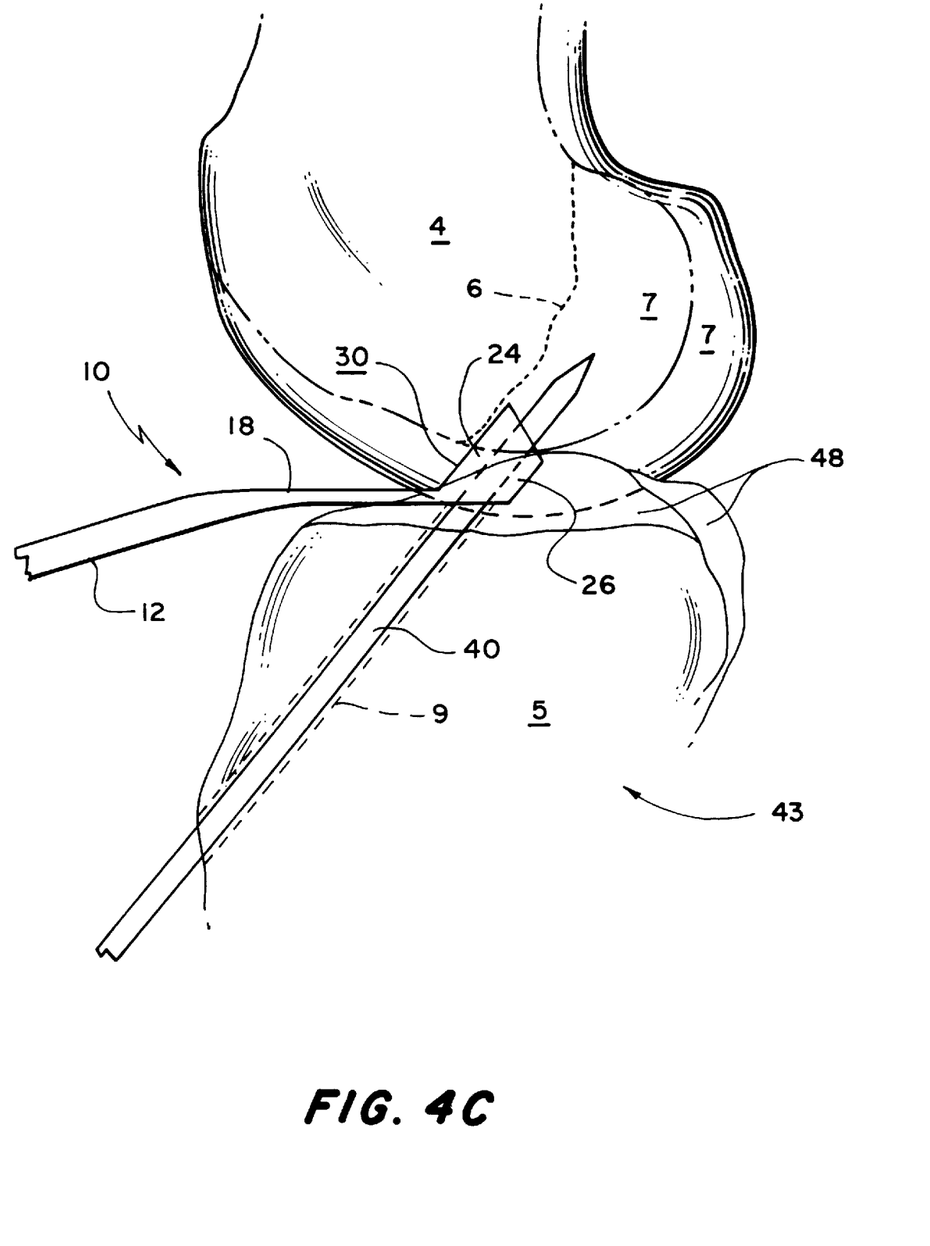

FIGS. 4A–4C illustrate an approach for using impingement device 10 in determining possible impingement of a replacement ACL graft. Referring to FIGS. 4A and 4C early in the ACL reconstruction procedure, drill-tipped guidewire 40 is passed from an anterior surface 46 of tibia 5 through the bone at an angle oblique to the long axis of tibia 5 into the knee joint. Preferably, the lower leg (containing tibia 5) is flexed in the direction of arrow 54. Referring to FIG. 4B, the impingement device 10 is next inserted through an incision in the skin and soft tissue into the knee joint and attached to guidewire 40 via groove 26 of head 24. Again, the lower leg is preferably flexed to allow device 10 access to guidewire 40. With the knee flexed as shown, impingement surface 30 of head 24 is spaced from the surface of roof 6 of the intercondylar notch. In this example, only the right half of device 10 is used in the flexed left knee joint so that shaft 12 protrudes anteriorly from the knee and does not interfere with tibia 5 or femur 4. If the ACL reconstruction were to be performed on the right knee, the left half of device 10 must be used. Once device 10 is attached to guidewire 40, the impingement surface 30 of device 10 is now a surrogate for the exterior surface of ACL graft 1.

Referring to FIG. 4C, the lower leg containing tibia 5 is then fully extended in the direction indicated by arrow 43. Possible impingement is determined by observing contact between roof 6 of the intercondylar notch of femur 4 and impingement surface 30 of device 10. If there is no contact between impingement surface 30 and roof 6, the surgeon can be confident that forming bone passages along the hole formed by guidewire 40, followed by proper placement of the replacement ACL graft, will result in a successful procedure without impingement of the graft. On the other hand, if contact is made, the surgeon knows before drilling the bone passage through the tibia that there is a possible impingement problem if the tunnel is drilled at the position established by guidewire 40. In that case, the surgeon can avoid impingement by (1) removing and redrilling the guidewire in a new position, or (2) performing notch plasty on roof 6. However the surgeon rectifies the possible impingement problem, the position of hole 9 formed by guidewire 40, which defines the position of the finished tibial tunnel 3 (shown in FIG. 1), is a matter of surgeon choice.

Other embodiments are within the scope of the following claims.

Although the above embodiment is made from an integral piece of stainless steel, variants can be made from any number of suitable materials or consist of more than one piece.

Figure 5:
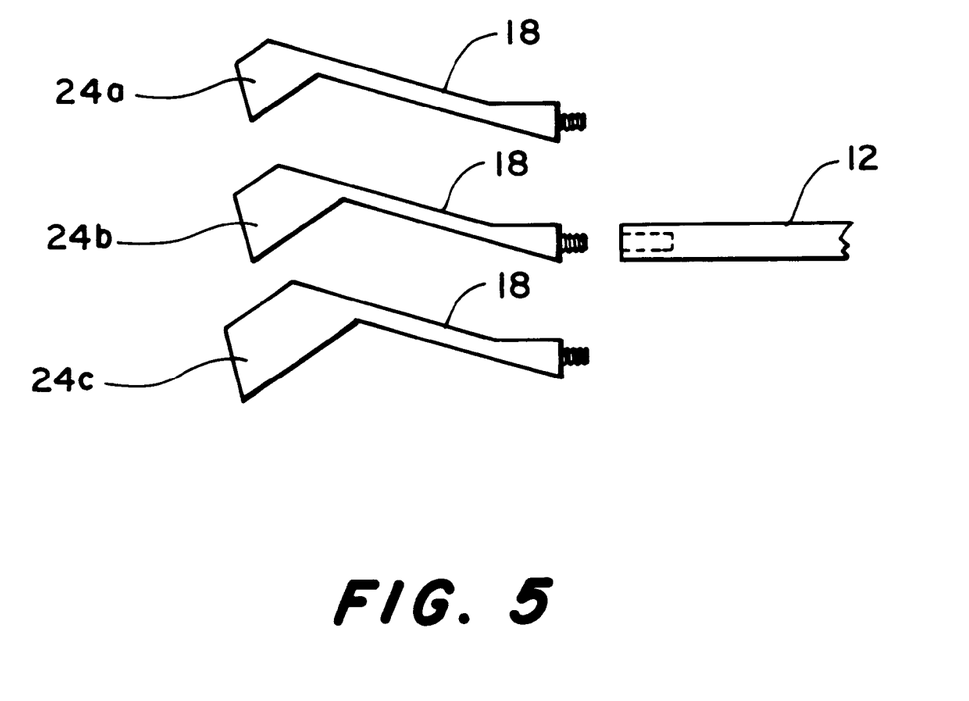
FIG. 5 shows a perspective view of one end of an impingement device having removable heads of different size.

Referring to FIG. 5, for example, a device can include a set of removable heads 24A, 24B, 24C of different size having different impingement surfaces or different pre-determined distances from the engagement passage axis. Heads 24A, 24B, 24C, include a screw portion 60 which is received within a corresponding threaded hole 62 formed within the distal end of shaft 12.

Moreover, other arrangements of slots may be formed or otherwise provided within the head of the impingement device to provide the spring-like "snap-on" engagement of the device to a guidewire. Indeed, in lieu of a slot arrangement, other approaches including magnetic means, may be used to reliably attach the device to a guidewire. Alternatively, the engagement passage can be a hole, in which case the device is slipped onto the end of the guidewire.

It is also appreciated that an impingement device may be suitably configured to determine possible impingement of other types of grafts in other joints.

What is claimed is:

1. A device for determining possible impingement of a replacement tissue graft with a portion of a bone at a joint, the replacement tissue graft of the type to be inserted and secured within a bone passage at the joint, the device comprising:

an elongated support shaft having a longitudinal axis;

a head disposed at a distal end of the support shaft and including:

an engagement passage having an axis, the engagement passage configured to engage a guidewire disposed within the bone, a detent mechanism configured to flexibly engage the guidewire in the passage, and an impingement surface corresponding to a shape of a portion of the replacement tissue graft, the impingement surface spaced from the axis of the passage by a range of pre-determined distances corresponding to a dimension of the tissue graft relative to the portion of the bone at the joint.

2. The device of claim 1, wherein the head includes a detent mechanism for engaging the passage with the guidewire.

3. The device of claim 1, wherein the head includes a slot and the detent mechanism includes at least one cantilever member defined by the slot.

4. The device of claim 1, wherein the engagement passage is a groove configured to be received along a side portion of the guidewire.

5. The device of claim 1, wherein the engagement passage is a hole configured to be received over a distal end of the guidewire.

6. The device of claim 1, wherein the support shaft includes a neck at the distal end, the neck having an axis offset from the longitudinal axis.

7. The device of claim 6, wherein the axis of the engagement passage is at an angle from the axis of the neck.

8. The device of claim 7, wherein the angle is in a range between about 45° and about 60°.

9. The device of claim 1, wherein the impingement surface corresponds to a shape of an anterior cruciate ligament graft.

10. The device of claim 1, wherein the pre-determined distance represents a dimension of a cross-section of the replacement tissue graft.

11. The device of claim 10, wherein the pre-determined distance is in a range between about 3 mm and about 6 mm.

12. The device of claim 1, wherein the impingement surface is rounded.

13. The device of claim 1, wherein the head comprises a material selected from the group consisting of stainless steel, titanium, and plastic.

14. The device of claim 1, wherein the support shaft further comprises a second head at a second distal end of the shaft, the second head including;

an engagement passage having an axis, the engagement passage configured to engage a guidewire disposed within the bone; and an impingement surface corresponding to a shape of a portion of the replacement tissue graft, the impingement surface spaced from the axis of the passage by a range of pre-determined distances corresponding to a dimension of the tissue graft relative to the portion of the bone at the joint.

15. A device for determining possible impingement of a replacement tissue graft with a portion of a bone at a joint, the replacement tissue graft of the type to be inserted and secured within a bone passage at the joint, the device comprising:

an elongated support shaft having a longitudinal axis;

a first head disposed at a distal end of the support shaft and including:

an engagement passage having an axis, the engagement passage configured to engage a guidewire disposed within the bone, a detent mechanism configured to flexibly engage the guidewire in the passage, and an impingement surface corresponding to the shape of a portion of the replacement tissue graft, the impingement surface spaced from the axis of the passage by a range of pre-determined distances corresponding to a dimension of the tissue graft relative to the portion of the bone at the joint; and a second head at a second distal end of the support shaft, wherein the second head is configured as a mirror image of the first-mentioned head relative to a plane normal to the longitudinal axis of the shaft.

16. The device of claim 1, wherein the head is configured to be removably detached from the distal end of the support shaft.

17. The device of claim 16 further comprising a plurality of heads, each head a different size and configured to be removably detached from the distal end of the support shaft.

18. A method of determining possible impingement of a replacement tissue graft with a portion of a bone at a joint, the replacement tissue graft of the type to be inserted and secured within a bone passage at the joint, comprising the steps of:
- (a) inserting an end of a guidewire into the bone at the joint;
- (b) positioning a device having an engagement passage to engage the end of the guidewire, the device having an impingement surface;
- (c) extending the joint to full extension; and
- (d) determining if the impingement surface of the device contacts the portion of the bone, thereby determining possible impingement of the replacement tissue graft with the portion of the bone at the joint.

19. The method of claim 18, further comprising removing bone from an area of impingement of the bone at the joint and repeating steps (b)–(d).

20. The method of claim 18, wherein the device includes a head with the engagement passage formed therein, the method further comprising forming the head to have a shape corresponding to a shape of an anterior cruciate ligament graft.

21. The method of claim 18, further comprising forming the bone passage after the determining step.

22. The method of claim 18 further comprising, after determining if the impingement surface of the device contacts the portion of the bone, removing the device from the joint.

* * * * *